United States Patent [19]

Su

[11] Patent Number: 4,670,557

[45] Date of Patent: Jun. 2, 1987

[54] PROCESS FOR PREPARING HYDROXYMORPHOLINES

[75] Inventor: Wei-Yang Su, Austin, Tex.

[73] Assignee: Texaco Inc., White Plains, N.Y.

[21] Appl. No.: 902,552

[22] Filed: Sep. 2, 1986

[51] Int. Cl.⁴ .......................................... C07D 265/32
[52] U.S. Cl. .................................. 544/173; 544/178; 564/399; 564/475
[58] Field of Search .......................................... 544/173

[56] References Cited

U.S. PATENT DOCUMENTS 3,225,042 12/1965 Dillard et al. ....................... 544/173

Primary Examiner—Robert W. Ramsuer
Attorney, Agent, or Firm—Jack H. Park; Kenneth R. Priem; Cynthia L. Kendrick

[57] ABSTRACT

This invention relates to the reaction of aliphatic epoxides and primary amines to form hydroxymorpholines or morpholines by a process comprising reacting said epoxide and primary amine in the presence of a ruthenium-containing compound plus a tertiary phosphine.

13 Claims, No Drawings

PROCESS FOR PREPARING HYDROXYMORPHOLINES

FIELD OF THE INVENTION

This invention relates to a process for the preparation of novel hydroxymorpholines by reacting epoxides

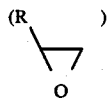

with primary amines.

More specifically, this invention concerns the reaction of epoxides such as propylene oxide and 1,2-epoxybutane with alkylamines to yield products such as 4-t-butyl-2,6-dimethyl-2-hydroxymorpholine and 2-hydroxyl, 2,6-dimethyl-4-alkylmorpholines. These t-butyl hydroxymorpholine derivatives can be used as epoxy resin light stabilizing agents.

BACKGROUND OF THE INVENTION

The manufacture of morpholines by heating diethanolamines or diisopropanolamines with excess sulfuric acid and then treating the mixture with alkalis has been disclosed. (U.S. Pat. No. 2,776,972) This process has the disadvantage that it produces by-product salts that are difficult to dispose of.

The cyclization of bis-(2-hydroxyalkyl)-amines by vapor phase dehydration over aluminum oxide and silicate catalysts at temperatures of from 300°–400° C. is disclosed in U.S. Pat. No. 2,597,260. This method produces large amounts of by-products.

A process for the production of morpholines is disclosed in U.S. Pat. No. 3,225,042, to Eli Lilly. In that process a methylenemorpholine is contacted with water, preferably in the form of a mixture with a water-miscible organic solvent.

In an article in J. Org. Chem. (1963), 28, 448, Dillard et al. discuss various methods of preparing substituted N-(2-hydroxyalkyl)propargylamines; and, their cyclization and subsequent hydrogenation to various morpholine derivatives is reported.

U.S. Pat. No. 4,068,077 discloses a process for the manufacture of morpholines by conversion of N-substituted bis-(2-hydroxyalkyl)amines. The cyclization of the N-substituted bis-(2-hydroxyalkyl)amines can be carried out in the presence of conventional catalysts containing aluminum, phosphorous, magnesium and calcium. In the second step suitable catalysts for hydrogenation are metals of Groups Ib, VIa and VIII of the Periodic Table.

These references do not appear to discuss the synthesis of new hydroxymorpholine compounds, nor do they discuss a novel process comprising reacting epoxides with primary amines in the presence of a ruthenium catalyst.

It would be an advance in the art to devise a process for producing hydroxymorpholines using mild conditions and a relatively inexpensive catalyst which did not produce large amounts of pollutants or unwanted by-products. In addition it would be desirable to devise a system whereby product distribution can be affected by varying reaction conditions or steric hindrance of amines.

These hydroxymorpholines could be useful as epoxy resin light stabilizing agents. Other hydroxymorpholines, represented by the formula

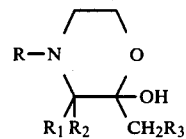

have been reported to have the valuable pharmacological property of antimicrobial action.

SUMMARY OF THE INVENTION

In accordance with the present invention epoxides and primary amines are reacted in the presehce of a ruthenium-containing compound to produce hydroxymorpholines at a temperature of 100°–400° C. and a pressure of atm to 1000 psi. The distribution of products can be controlled by varying the reaction conditions or steric hindrance of amines. The yield of hydroxymorpholine reaches as high as 61%. (Example IV) The yield of morpholine is as high as 90%. (Example VII)

DETAILED DESCRIPTION OF THE INVENTION

In the narrower and more preferred practice of this invention hydroxymorpholines are prepared from epoxides and primary amines by a process which comprises reacting said epoxide and primary amine in the presence of a ruthenium-containing compound with a phosphine ligand and a solvent at a pressure of at least 50 psi and a temperature of at least 150° C. until there is substantial formation of the desired hydroxymorpholines.

The general reaction for reacting epoxides with primary amines in the presence of a ruthenium catalyst under mild conditions can be represented by:

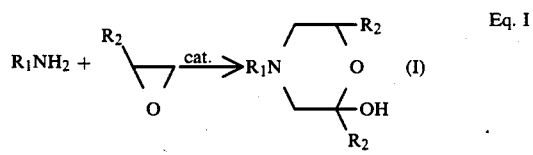

Eq. I

All the hydroxymorpholines reported in the invention are new compounds.

Other hydroxymorpholines represented by the formula II have been reported to have valuable pharmacological antimicrobial action in standard laboratory tests (See U.S. Pat. No. 3,225,042). In addition the hydroxymorpholine compounds can be potentially useful as epoxy resin light stabilized agents.

In the process of this invention the general equation can be represented by Eq. I above. However, the product distribution depends on steric hindrance of the amines and the temperature. In general, for less hindered amines or at higher temperatures, the reaction produced a higher yield of morpholines represented by Structure III. On the other hand, for more hindered amines or at a lower temperature, hydroxymorpholines of Structure I are obtained to a higher extent.

Eq. II

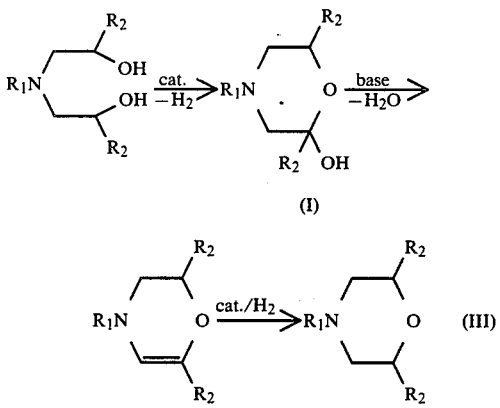

Recovery of the hydroxymorpholine and by-products from the reaction product can be carried out in any convenient or conventional manner such as by distillation, extraction etc.

In general, the components of the reaction mixture, including the epoxide, primary amine compound, ruthenium-containing compound and solvent may be added in any sequence as long as good agitation is employed to provide a good dispersion or a homogeneous reaction mixture. For example, the following represent some variations insofar as the addition of catalyst components, solvent and epoxide addition that can be made without departing from the inventive process. These modifications include:

1. The catalyst may be preformed and added to the solvent prior to addition of the epoxide, alkylamine and other reactants.

2. Preferably, to minimize stability problems with the catalyst, the catalyst is best formed in situ, usually by mixing the solvent, epoxide and amine followed by the addition of the ruthenium-containing compound and phosphorous-containing compound to form the reaction mixture.

3. After using either variation 1 or 2 the catalyst containing reaction mixture is heated until the product is formed.

The reactants used in the process of this invention comprise an epoxide and an alkylamine.

The catalyst system comprises a ruthenium-containing compound used with a phosphine ligand and a solvent.

The ruthenium-containing compound to be used in the catalyst in practice of this invention may be chosen from a wide variety of organic or inorganic compounds, complexes, etc. as will be shown and illustrated below. It is only necessary that the catalyst precursor actually employed contain said ruthenium in any of its ionic states. The actual catalytically active species is then believed to comprise ruthenium in complex combination with one or more phosphine promoters and a solvent.

The ruthenium catalyst precursors may take many different forms. For instance, the ruthenium may be added to the reaction mixture in an oxide form, as in the case of, for example, ruthenium(IV) oxide hydrate. Alternatively, it may be added as the salt of a mineral acid, as in the case of ruthenium(III) chloride hydrate, ruthenium(III) bromide, ruthenium(III) iodide, tricarbonyl ruthenium(II) iodide, anhydrous ruthenium(III) chloride and ruthenium nitrate, or as the salt of a suitable organic carboxylic acid, such as, for example, ruthenium(III) acetate, ruthenium naphthenate, ruthenium valerate and ruthenium complexes with carbonyl-containing ligands, such as ruthenium(III) acetylacetonate. The ruthenium may also be added to the reaction zone as a carbonyl or hydridocarbonyl derivative. Here, suitable examples include triruthenium dodecacarbonyl and other hydridocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

Preferred ruthenium-containing compounds include ruthenium salts of a mineral acid. Among these, particularly preferred is ruthenium trichloride.

The preferred catalyst comprises a ruthenium source plus a tertiary phosphine such as a trialkyl phosphine or a triarylphosphine such as triphenylphosphine. A preferred example is ruthenium trichloride in the presence of an excess of tributylphosphine.

Suitable tertiary phosphine components comprising the preferred catalyst formulations may contain one or more trivalent phosphorus atoms per molecule, bonded to alkyl, aryl, alkaryl and aralkyl radicals, or mixtures thereof. Specific examples of such tertiary phosphines include tri-n-butylphosphine, tri-sec-butylphosphine, trimethylphosphine, triethylphosphine, tri-c-hexylphosphine, triphenylphosphine, tri-p-tolylphosphine, benzyldiphenylphosphine, tri-p-methoxyphenylphosphine, as well as
1,2-bis(dibenzylphosphino)ethane
1,2-bis(di-n-butylphosphino)ethane
1,2-bis(dicyclohexylphosphino)ethane
1,2-bis(diethylphosphino)ethane
1,2-bis(dimethylphosphino)ethane
1,4-bis(diphenylphosphino)butane
1,2-bis(diphenylphosphino)ethane
1,6-bis(diphenylphosphino)hexane
1,5-bis(diphenylphosphino)pentane
1,3-bis(diphenylphosphino)propane
1,2-bis(di-n-propylphosphino)ethane
n-butyldiphenylphosphine
diethylphenylphosphine
di-n-hexylphenylphosphine
ethyldiphenylphosphine
hexyldiphenylphosphine
tribenzylphosphine, triisobutylphosphine,
tri-n-propylphosphine.

In the practice of this invention epoxides are reacted with primary amines to give the desired hydroxymorpholine products (eq. I). Suitable epoxide reactants should be aliphatic or aromatic oxiranes, but preferably aliphatic oxiranes that contain three to 20 carbons per molecule. Said aliphatic oxiranes may be substituted at both the one and two carbon positions.

Examples of aliphatic oxiranes that are suitable reactants in the desired syntheses of hydroxymorpholines include propylene oxide, 1,2-epoxybutane, 2,3-epoxybutane, 1,2-epoxyoctane and 1,2-epoxydodecane.

The primary amine coreactant in the generation of hydroxymorpholines may be an aliphatic amine containing one to 20 carbon atoms, or an aromatic or cycloaliphatic amine containing six to 20 carbon atoms per molecule.

Examples of primary amines that are suitable reactants in the desired syntheses include, tert-butylamine, iso-propylamine, n-propylamine, methylamine, ethyl-amine, dodecylamine, aniline, toluidine, cyclohexylamine and the phenyldiamines.

In the first embodiment of the process of this invention an epoxide and an alkyl amine are reacted in the presence of a solubilized ruthenium catalyst, a tertiary phosphine and a solvent to form hydroxymorpholines and morpholines. Hydroxymorpholines will include 4-tert-butyl-2,6-dimethyl-2-hydroxymorpholine; 4-isopropyl-2,6-dimethyl-2-hydroxymorpholine; 4-n-propyl-2,6-dimethyl-2-hydroxymorpholine; and, 4-phenyl-2,6-dimethylmorpholine among others. Morpholines will include 4-n-propyl-2,6-dimethylmorpholine; 4-tert-butyl-2,6-dimethylmorpholine and 4-phenyl-2,6-dimethylmorpholine among others. The reaction can be represented by equations I and II above:

The reaction allows up to greater than 99% conversion of amine and up to 90% or greater yield of a morpholine or 90% or greater yield of a hydroxymorpholine.

The temperature range which can be employed for the reaction is a variable which is dependent upon experimental factors including the particular epoxide and alkylamine compounds employed, the total pressure, the concentrations of reactants and catalyst, and particularly the choice of ruthenium catalyst and solvent, among other things. Using propylene oxide or 1,2-epoxybutane and a primary amine, such as tert-butylamine as the substrate with $RuCl_3$-$PBu_3$ as a representative catalyst, an operable range is from about 100° C. to 400° C. when superatmospheric pressures of greater than 50 psig are employed. A narrower range of 150° C. to 220° C. represents the preferred temperature range when the aforementioned epoxides are reacted. As mentioned earlier the yield of reaction products can be affected by steric hindrance or reaction conditions. Where the desired products are hydroxymorpholines the preferred temperature should be milder, in the range of 150° C. to 190° C. Where the desired product is a morpholine the preferred temperature will be higher, around 200° C. to 240° C.

The pressure range which can be employed for the reaction is a variable which is also dependent on the factors mentioned above. Using $RuCl_3$-tributylphosphine and 1,4-dioxane as a representative catalyst and solvent, and propylene oxide and t-butylamine as the substrate, an operable pressure range is from about atm to 1000 psig, or more, when a temperature range of from about 100° to 400° C. is employed. A narrower range of from 50 to 350 psig represents the preferred pressure range when the narrower temperature range of 150° C. to 220° C. is employed.

As previously indicated in the analogous discussion on temperatures and pressures required in the reaction, experimental variables are important in arriving at reaction times. Generally, substantial conversions (up to 99%) of the amines to hydroxymorpholines can almost always be accomplished within 10 hours, with 2 to 6 hours representing the more usual reaction time interval.

In the process of this invention the molar ratio of ruthenium-containing compound to the phosphine ligand is significant. The experimental work performed indicates that an excess of ligand of about at least 3 moles of trialkylphosphine for each mole of ruthenium-compound complex is preferred for good selectivity. Generally a ratio of from 1 to 500 moles of tertiary phosphine for each mole of ruthenium-containing compound has been established to yield the hydroxymorpholine product. Preferably a ratio of 3 to 100 moles per mole of ruthenium compound is employed for good yields of hydroxymorpholine. This preferred ratio is based upon the reaction where propylene oxide and t-butylamine are used as the substrates.

Experimental work indicates that an initial molar ratio of 100 moles to 300 moles of amine per mole of ruthenium catalyst can be employed in most instances. The minimal ratio would be about 0.001 moles of catalyst per mole of amine.

The novel reaction is run most conveniently in the presence of a solvent. The solvent useful in the process of this invention is an oxygenated hydrocarbon, i.e., a compound composed only of carbon, hydrogen and oxygen and one in which the only oxygen atoms present are in ether groups or ester groups. Generally, the oxygenated hydrocarbon will contain 3 to 14 carbon atoms and preferably a maximum of 7 oxygen atoms. The solvent must be substantially inert under reaction conditions.

Preferred ester type solvents are the aliphatic and acrylic carboxylic acid monoesters as exemplified by butyl acetate, methyl benzoate, isopropyl iso-butyrate, and propyl propionate as well as dimethyl adipate, dimethylphthalate and dioctylphthalate. Ethers which may be utilized as solvents include cyclic, acyclic and heterocyclic materials. Preferred ethers are the aliphatic ethers such as tetraglyme and triglyme and heterocyclic ethers, as illustrated by 1,4-dioxane and 1,3-dioxane. Other suitable ether solvents include isopropyl propyl ether, diethylene glycol dibutyl ether, dibutyl ether, ethyl butyl ether, diphenyl ether, heptyl phenyl ether, anisole, tetrahydrofuran, etc.

The most preferred solvent in the reaction to produce hydroxymorpholines was 1,4-dioxane. Another solvent which worked well, especially in preparing morpholines was tetraglyme.

Products, including 4-tert-butyl-2,6-dimethyl-2-hydroxymorpholine and 2,4,6-trimethylmorpholine may be isolated by the usual chemical or physical techniques, such as distillation, solvent extraction, chromatography, etc. Identification is by nuclear magnetic resonance and infra-red spectroscopy. Unless otherwise specified all percentages are by weight and all temperatures are in centigrade rather than fahrenheit.

Yield, as defined herein, represents the efficiency in catalyzing the desired reaction relative to other undesired reactions. In this instance synthesis of hydroxymorpholines and morpholines is the desired conversion. Yield is expressed as a molar percentile, and is calculated by determining the molar amount of, for example, 4-tert-butyl-2,6-dimethyl-2-hydroxymorpholine or 2,4,6-trimethylmorpholine product formed, divided by the molar amount of primary amine charged and multiplying the quotient obtained by 100.

Having described the inventive process in general terms, the following examples are submitted to supply specific and illustrative embodiments.

EXAMPLE 1

A 300-ml stirred autoclave with pyrex liner was charged with a mixture of t-butylamine (14.6 g, 0.2 mol), propylene oxide (34.8 g, 0.6 mol), tributylphosphine (1.6 ml), ruthenium(III) trichloride hydrate (0.520 g) and 1,4-dioxane (20 ml). The reactor was sealed and purged of air. The reaction was heated to 180° C. and held for five hours. During the process, the pressure went up to 250 psi. The reaction was allowed to cool to room temperature. The solvent was removed at reduced pressure. The products were distilled to obtain a 52% yield of 4-tert-butyl-2,6-dimethyl-2-hydroxymorpholine and a 12% yield of N-tert-butyl-bis-(2-hydroxypropyl)amine. There is only a small amount of 4-tert-butyl-2,6-dimethylmorpholine (<1%) found in this reaction.

EXAMPLE 2

Isopropylamine (11.8 g, 0.2 mol) and propylene oxide (34.8 g, 0.6 mol) were subjected to a reaction as described in Example 1 above, except that the reaction temperature was 165° C. A 32% yield of 4-isopropyl-2,6-dimethyl-2-hydroxymorpholine was obtained along with 50% of N-isopropyl-bis-(2-hydroxypropyl)amine.

EXAMPLE 3 n-Propylamine (11.8 g, 0.2 mol) and propylene oxide (34.8 g, 0.6 mol) were subjected to a reaction as described in Example 1 above. A 17% yield of 4-n-propyl-2,6-dimethyl-2-hydroxymorpholine and 43% yield of 4-n-propyl-2,6-dimethylmorpholine were obtained along with a 25% yield of N-n-propyl-bis-(2-hydroxypropyl)amine.

EXAMPLE 4 tert-Butylamine (17.0 g, 0.23 mol) and 1,2-epoxybutane (50 g, 0.69 mol) were subjected to a reaction as described in Example 1 above. A 61% yield of 4-tert-butyl-2,6-diethyl-2-hydroxymorpholine was obtained along with a 30% yield of N-tert-butyl-bis-(2-hydroxybutyl)amine.

EXAMPLE 5 tert-Butylamine (14.6 g, 0.2 mol) and propylene oxide (34.8 g, 0.6 mol) were subjected to a reaction as described in Example 1 above except that the reaction temperature was 220° C. A 54% yield of 4-tert-butyl-2,6-dimethylmorpholine and a 14% yield of 4-tert-butyl-2,6-dimethyl-2-hydroxymorpholine were obtained along with an 8% yield of N-tert-butyl-bis-(2-hydroxypropyl)amine.

EXAMPLE 6

Aniline (18.6 g, 0.2 mol) and propylene oxide (34.8 g, 0.6 mol) were subjected to a reaction as described in Example 1 above. A 50% yield of 4-phenyl-2,6-dimethyl-2-hydroxymorpholine and a 15% yield of 4-phenyl-2,6-dimethylmorpholine were obtained along with a 10% yield of N-phenyl-bis-(2-hydroxypropyl)amine.

EXAMPLE 7

A 300 ml stirred autoclave with pyrex liner was charged a mixture of N-methyldiisopropanolamine (60 g, 0.41 mol), tributylphosphine (1.6 ml), ruthenium trichloride (0.520 g) and tetraglyme (30 ml). The reactor was sealed and purged of air. The reaction was heated to 180° C. and held for three hours. The reaction was allowed to cool to room temperature. The reaction mixtures were distilled to obtain a 90% yield of 2,4,6-trimethylmorpholine.

EXAMPLE 8

Triphenylphosphine (2.0 g) was substituted for tributylphosphine in the reaction described in Example 7 above. A 60% yield of 2,4,6-trimethylmorpholine was obtained.

What is claimed is:

1. A process for preparation of hydroxymorpholines by the reaction of aliphatic epoxides containing 3 to 20 carbon atoms, with primary amines in the presence of a ruthenium-containing compound with a phosphine ligand at a temperature of to 150° C. to 190° C. and a pressure of at least one atmosphere.

2. The process of claim 1 wherein the ruthenium-containing compound is selected from the group consisting of ruthenium salts of mineral acids, ruthenium salts of an organic carboxylic acid, ruthenium oxide and ruthenium complexes with carbonyl-containing ligands as well as ruthenium carbonyls and hydrocarbonyls.

3. The process of claim 2 wherein the ruthenium compound is ruthenium(III) trichloride hydrate.

4. The process of claim 1 wherein the phosphine ligand contains one or more trivalent phosphorus atoms per molecule, bonded to alkyl, aryl, alkaryl and aralkyl radicals, or mixtures thereof.

5. The process of claim 4 wherein the tertiary phosphine is selected from the group including tri-n-butylphosphine and triphenylphosphine.

6. The process of claim 1 wherein the aliphatic epoxide is selected from the group consisting of propylene oxide and 1,2-epoxybutane.

7. The process of claim 1 wherein the primary amine is selected from the group consisting of aliphatic amines, aromatic amines and cycloaliphatic amines, containing one to 20 carbon atoms per molecule.

8. The process of claim 7 wherein the primary amine is selected from the group consisting of tert-butylamine, methylamine, isopropylamine, n-propylamine and aniline.

9. The process of claim 1 wherein the desired synthesis of hydroxymorpholines is conducted in the presence of a solvent.

10. The process of claim 9 wherein the solvent is selected from the group including aliphatic and heterocyclic ethers.

11. The process of claim 10 wherein the solvent is selected from the group including 1,4-dioxane and tetraglyme.

12. The process of claim 1 wherein the pressure is 50 psi to 350 psi.

13. A process for preparing 4-tert-butyl-2,6-dimethyl-2-hydroxymorpholine which comprises reacting a mixture of propylene oxide and t-butylamine in the presence of a ruthenium trichloride catalyst, excess phosphine ligand and a solvent at a temperature of 150° C. to 190° C. and a pressure of at least 50 psi.

* * * * *

UNITED STATES PATENT AND TRADEMARK OFFICE
CERTIFICATE OF CORRECTION

PATENT NO. : 4,670,557
DATED : June 2, 1987
INVENTOR(S) : Wei-Yang Su

It is certified that error appears in the above-identified patent and that said Letters Patent is hereby corrected as shown below:

Claim 5, Col. 8, line 28 delete "tertiary".

Signed and Sealed this

Thirteenth Day of October, 1987

Attest:

DONALD J. QUIGG

*Attesting Officer*   *Commissioner of Patents and Trademarks*